US008858503B2

(12) United States Patent
Burkholz et al.

(10) Patent No.: US 8,858,503 B2
(45) Date of Patent: Oct. 14, 2014

(54) TIP SHIELD WITH GRIPPING SURFACES AND GUARD FEATURES (75) Inventors: Jonathan Karl Burkholz, Salt Lake City, UT (US); S. Ray Isaacson, Roy, UT (US); Jeffrey C. O'Bryan, Murray, UT (US); Aaron Wang, Salt Lake City, UT (US); Wade A. Powell, Lexington, KY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 79 days.

(21) Appl. No.: 12/337,482

(22) Filed: Dec. 17, 2008
(Under 37 CFR 1.47)

(65) Prior Publication Data
US 2009/0163871 A1    Jun. 25, 2009

Related U.S. Application Data (60) Provisional application No. 61/016,157, filed on Dec. 21, 2007.

(51) Int. Cl.
*A61M 5/178* (2006.01)
*A61M 25/06* (2006.01)
*A61M 5/32* (2006.01)

(52) U.S. Cl.
CPC ....... *A61M 25/0606* (2013.01); *A61M 25/0618* (2013.01); *A61M 5/3202* (2013.01); *A61M 25/0637* (2013.01)
USPC ............. 604/164.08; 604/164.07; 604/165.01

(58) Field of Classification Search
USPC .......... 604/158, 162, 164.01, 164.04, 164.07, 604/164.08, 165.01–165.04, 263
See application file for complete search history.

(56) References Cited

U.S. PATENT DOCUMENTS

| 4,762,516 A | 8/1988 | Luther et al. |
| 4,950,252 A | 8/1990 | Luther et al. |
| 4,964,854 A | 10/1990 | Luther |
| 5,000,740 A | 3/1991 | Ducharme et al. |
| 5,051,109 A | 9/1991 | Simon |
| 5,205,829 A | 4/1993 | Lituchy |
| 5,215,528 A | 6/1993 | Purdy et al. |
| 5,279,591 A | 1/1994 | Simon |
| 5,312,359 A | 5/1994 | Wallace |
| 5,328,482 A | 7/1994 | Sircom et al. |
| 5,407,431 A | 4/1995 | Botich et al. |
| 5,458,658 A | 10/1995 | Sircom |
| 5,533,974 A | 7/1996 | Gaba |
| 5,601,536 A | 2/1997 | Crawford et al. |

(Continued)

FOREIGN PATENT DOCUMENTS

| EP | 0 554 841 A1 | 8/1993 |
| GB | 2 292 525 A | 2/1996 |

(Continued)

*Primary Examiner* — Nathan R Price
(74) *Attorney, Agent, or Firm* — Jeanne Lukasavage; Craig Metcalf; Kirton McConkie (57) ABSTRACT An asymmetrical gripping surface is incorporated into a needle shield of an intravenous catheter assembly. The asymmetrical gripping surface provides a gripping position nearer the catheter adapter, catheter and needle tip for improved balance and control of the catheter assembly during insertion of the catheter. Additionally, the asymmetrical gripping surfaces include a guard feature to prevent a user's unintended contact with various components of the catheter assembly whereby the contact may result in an undesirable "over the bevel" condition.

20 Claims, 6 Drawing Sheets

(56) References Cited

U.S. PATENT DOCUMENTS

| | | | |
|---|---|---|---|
| 5,718,688 A | 2/1998 | Wozencroft | |
| 5,910,132 A | 6/1999 | Schultz | |
| 6,001,080 A | 12/1999 | Kuracina et al. | |
| 6,004,294 A | 12/1999 | Brimhall et al. | |
| 6,186,984 B1 | 2/2001 | Fukutomi | |
| 6,217,587 B1 | 4/2001 | Tsuruta | |
| 6,234,999 B1 | 5/2001 | Wemmert et al. | |
| 6,379,332 B1 | 4/2002 | Van Landuyt | |
| 6,379,333 B1 | 4/2002 | Brimhall et al. | |
| 6,425,884 B1 | 7/2002 | Wemmert et al. | |
| 6,475,189 B1 | 11/2002 | Lilley, Jr. | |
| 6,652,490 B2 | 11/2003 | Howell | |
| 6,730,062 B2 | 5/2004 | Hoffman et al. | |
| 6,749,588 B1 | 6/2004 | Howell et al. | |
| 6,860,871 B2 | 3/2005 | Kuracina et al. | |
| 6,942,652 B1 | 9/2005 | Pressly, Sr. et al. | |
| 6,953,448 B2 | 10/2005 | Moulton et al. | |
| 6,981,965 B2 | 1/2006 | Luther et al. | |
| 7,226,434 B2 | 6/2007 | Carlyon et al. | |
| 7,238,169 B2 | 7/2007 | Takagi et al. | |
| 8,357,121 B2 * | 1/2013 | Burkholz | 604/164.01 |
| 2004/0092889 A1 | 5/2004 | Ferguson et al. | |
| 2004/0116864 A1 | 6/2004 | Boudreaux | |
| 2004/0186434 A1 | 9/2004 | Harding et al. | |
| 2004/0193112 A1 | 9/2004 | Glazier et al. | |
| 2004/0204681 A1 | 10/2004 | Thoresen et al. | |
| 2004/0225260 A1 | 11/2004 | Villa et al. | |
| 2004/0236288 A1 | 11/2004 | Howell et al. | |
| 2006/0015071 A1 | 1/2006 | Fitzgerald | |
| 2007/0179446 A1 | 8/2007 | Carrez et al. | |

FOREIGN PATENT DOCUMENTS

| | | |
|---|---|---|
| JP | 2003-199822 A2 | 7/2003 |
| WO | 98/53873 | 12/1998 |
| WO | 02/096494 A1 | 12/2002 |
| WO | 2004/091687 A2 | 10/2004 |

* cited by examiner

TIP SHIELD WITH GRIPPING SURFACES AND GUARD FEATURES

RELATED APPLICATIONS

This application claims the benefit of U.S. Provisional Application No. 61/016,157, filed Dec. 21, 2007, entitled TIP SHIELD WITH GRIPPING SURFACES AND GUARD FEATURES, which is incorporated herein by reference.

BACKGROUND OF THE INVENTION

The present invention relates to infusion devices, specifically to over-the-needle peripheral intravenous (IV) catheters. Specifically, the invention relates to peripheral IV catheters with a protective needle shield having gripping surfaces to allow a user to hold the device nearer the catheter and needle tip for increased stability and control during insertion. Catheters are widely used throughout the medical community for a wide range of procedures and treatments.

Catheters are commonly used for a variety of infusion therapies. Catheters are used for infusing fluid, such as normal saline solution, various medicaments, and total parenteral nutrition, into a patient, withdrawing blood from a patient, or monitoring various parameters of the patient's vascular system. A common type of intravenous (IV) catheter is an over-the-needle peripheral IV catheter. As its name implies, an over-the-needle catheter is mounted over an introducer needle having a sharp distal tip. At least the distal portion of the catheter tightly engages the outer surface of the needle to prevent peelback of the catheter and thus facilitate insertion of the catheter into the blood vessel. The catheter and the introducer needle are assembled so that the distal tip of the introducer needle extends beyond the distal tip of the catheter with the bevel of the needle facing up away from the patient's skin. The catheter and introducer needle are generally inserted at a shallow angle through the patient's skin into a blood vessel.

The process of placing a catheter requires careful balance and control over the catheter. Typically an IV catheter will be incorporated into a catheter assembly. The catheter assembly may include various components and sub-components to aid in the use and placement of the IV catheter. Typically a catheter assembly will provide a gripping surface to aid in griping and controlling the IV catheter during insertion. The gripping surface will commonly provide opposing gripping surfaces whereby a user may pinch and hold the device during insertion.

Rather than using the provided opposing gripping surfaces, a user will commonly reposition their grip to a "choked up" position. A "choked up" position allows a user to position their grip nearer the catheter and needle tip for increased stability during insertion. While this "choked up" position does provide for greater control, this position may result in a premature separation of the components of the catheter assembly. A premature separation of the catheter assembly may lead to the "over the bevel" condition in which the bevel portion of the needle tip is withdrawn into the catheter prior to sufficiently piercing the patient's skin.

An "over the bevel" condition may occur in at least two situations. First, the "choked up" position of the user's grip may wedge a portion of the user's fingers or thumb between various components of the catheter assembly thereby causing a premature separation. Second, the "choked up" position may remove a user's grip from the needle containing component of the catheter assembly. This means that upon contacting the patient with the bevel portion of the needle tip, the insertion force may cause the needle and the needle containing components to move in a direction opposite to the direction of insertion, thereby causing a premature separation. Both of these situations result in the undesirable "over the bevel" condition The "over the bevel" condition is disruptive to the insertion, as well as painful and potentially damaging to the patient. For example, if the bevel portion of the needle tip insufficiently pierces the skin prior to the "over the bevel" condition, the user must either increase the insertion force to widen the insufficient pierce or must cease the insertion attempt and control the patient's bleeding. In either instance, the experience is painful, ineffective, uncomfortable, and undesirable.

With such a need to maintain control and balance over the catheter and needle, it is not surprising that users prefer a "choked up" grip. Unfortunately, the convenience and control of the "choked up" position is outweighed by the high probability and risk of failed or painful insertion.

Accordingly, there is a need in the art for a catheter assembly incorporating a gripping surface that will allow users to position their grip in a balanced, "choked up" position without the risk of encountering an "over the bevel" condition. Such a gripping surface is disclosed herein.

BRIEF SUMMARY OF THE INVENTION

In order to overcome the limitations discussed above, the present invention relates to a new gripping surface that may be incorporated into a current catheter assembly. The new gripping surface allows a user to use a "choked up" grip without the risk of encountering an "over the bevel" condition. As is known in the art, traditional gripping surfaces are provided to aid a user in griping and controlling the catheter assembly during insertion of the catheter. The gripping surface of the current invention is designed to be used alone or in conjunction with current, traditional gripping surfaces and is designed to allow a "choked up" grip while preventing the "over the bevel" condition.

Unlike traditional gripping surfaces commonly located on an outer surface of the needle hub of the catheter assembly, the present invention is located on an outer surface of the needle shield, thereby providing a gripping surface closer to the catheter and introducer needle tip portions of the catheter assembly. As such, the current invention provides an optional gripping surface for safely repositioning a user's fingers and thumb nearer the catheter and introducer needle without causing an "over the bevel" condition. Accordingly, if a user repositions their grip to the gripping surface of the needle shield, the new gripping surface will provide the user with improved control and balance over the prior art.

The needle shield generally comprises a needle port and a housing wherein the housing may be modified to include a safety feature or other device for retaining the tip of the introducer needle following insertion of the catheter. An outer surface of the needle shield comprises a first and second gripping surface wherein the gripping surfaces oppose one another. A first gripping surface is provided to accommodate the contours of a user's opposable digit, such as the user's thumb, wherein the first gripping surface is sized and positioned to permit only a portion of the user's thumb to fit or occupy the first gripping surface.

The catheter assembly is configured such that a wing portion of the needle hub overlaps a portion of the needle shield such that the wing portion of the needle hub abuts the first gripping surface. The wing portion and the first gripping surface provide a contact surface for accommodating a second portion of the user's thumb. Thus, the user simultaneously contacts the needle shield and the needle hub. This simultaneous contact of the user's thumb serves as a link or bridge between the needle shield and the needle hub thereby preventing a premature separation of the components during insertion of the catheter.

A second gripping surface is also provided to accommodate the contours of a user's first non-opposable digit, such as the user's index finger. The second gripping surface is sized and positioned to allow various positioning of the user's index finger. For example, the second gripping surface permits a user's index finger to be positioned opposite the user's thumb thereby forming a symmetrical, balanced grip. With the user's index finger in a balanced, symmetrical position, the design of the second gripping surface ensures that a first portion of the user's index finger contacts the second gripping surface, while a second portion of the user's index finger contacts a wing portion of the needle hub. As such, the user's index finger serves to link together the needle shield and the needle hub during insertion, thereby preventing premature separation, or an "over the bevel" condition.

Additionally, a user's index finger may grip a portion of the second gripping surface in an asymmetrical position closer to the catheter adapter thereby forming an imbalanced, asymmetrical grip. To balance this imbalanced, asymmetrical grip, a user's second non-opposable finger, such as a middle finger, is positioned on a gripping surface of the needle hub. The addition of the middle finger balances the catheter assembly and overcomes any undesirable rotational force created by the imbalanced, asymmetrical grip. The positioning and combined contact of the user's thumb, index finger, and middle finger serve to link together the needle shield and needle hub of the catheter assembly. As such an "over the bevel" condition or premature separation of the needle shield and the needle hub is prevented.

Additional features of the current invention include the addition of a guard surface or feature to the first and second gripping surfaces. Specifically, the first and second gripping surfaces may include a guard surface whereby a portion of the first and second gripping surfaces is extended outwardly, thereby preventing a user's finger and thumb from inadvertently contacting a portion of the catheter assembly. For example, the first gripping surface may include a guard surface which prevents a user's thumb from contacting an access port of the catheter adapter. As such, the user's thumb is unable to advance the catheter adapter independent of the needle shield creating an "over the bevel" condition. Additionally, the second gripping surface may include a guard surface whereby the user's index finger is prevented from contacting a catheter wing of the catheter adapter. As such, the user's thumb is unable to advance the catheter independent of the needle shield creating an "over the bevel" condition.

One embodiment of the present invention includes a needle shield comprising a first and second gripping surface. The first and second gripping surfaces further include a guard surface as described above. Additionally, the first and second gripping surface may provide for a two-point balanced, symmetrical grip of the needle shield, as well as a three-point balanced, asymmetrical grip of the needle shield. The present invention may also be modified to work in conjunction with other components of a catheter assembly. For example, the housing of the needle shield may be modified to include alignment tabs for compatibly engaging an alignment groove of a separate component. Additionally, the first and second gripping surfaces or the guard surfaces of the needle shield may be modified to control a user's contact with additional features of the catheter assembly.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
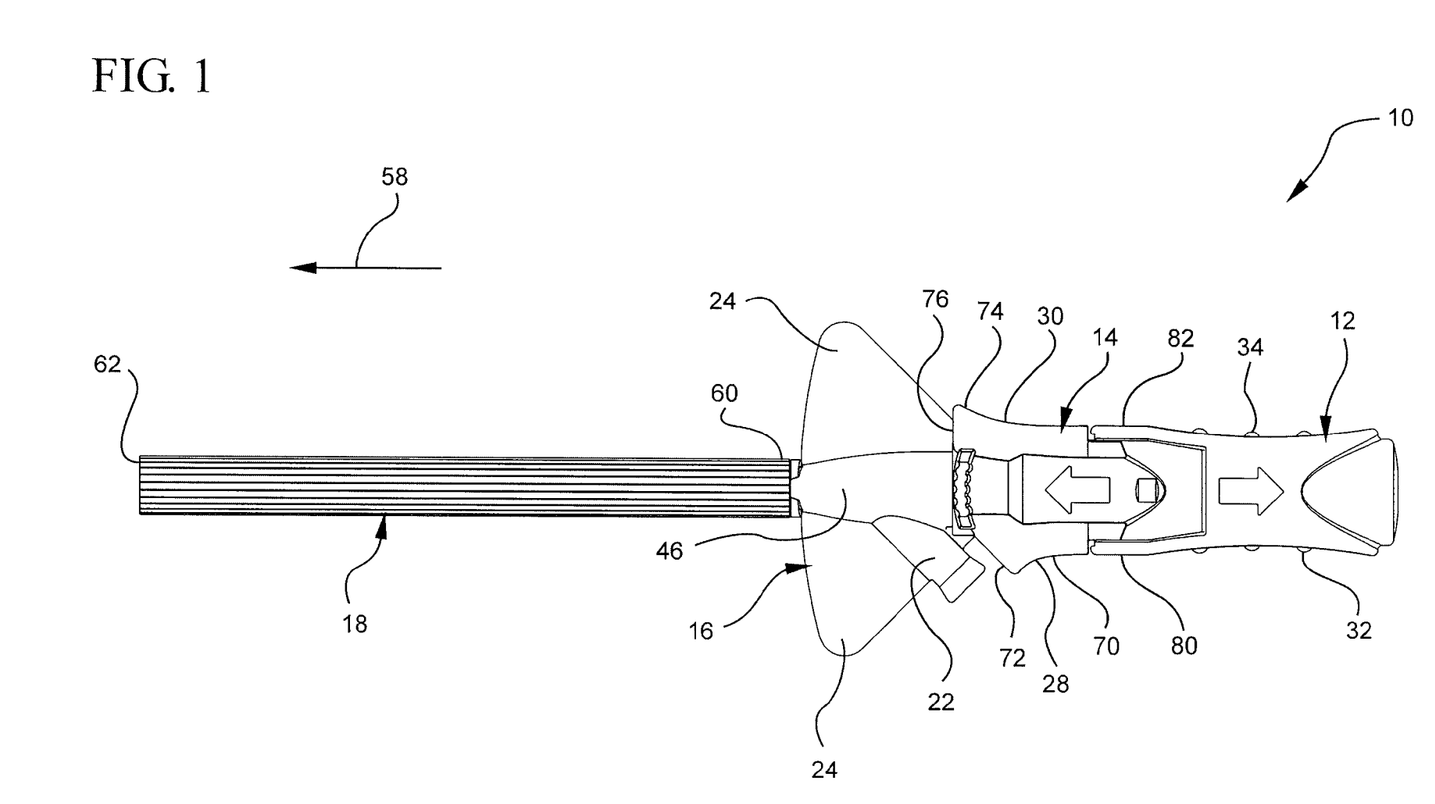
FIG. 1 is a perspective top view of a catheter assembly incorporating multiple gripping surfaces and guard features of the current invention.
Figure 2:
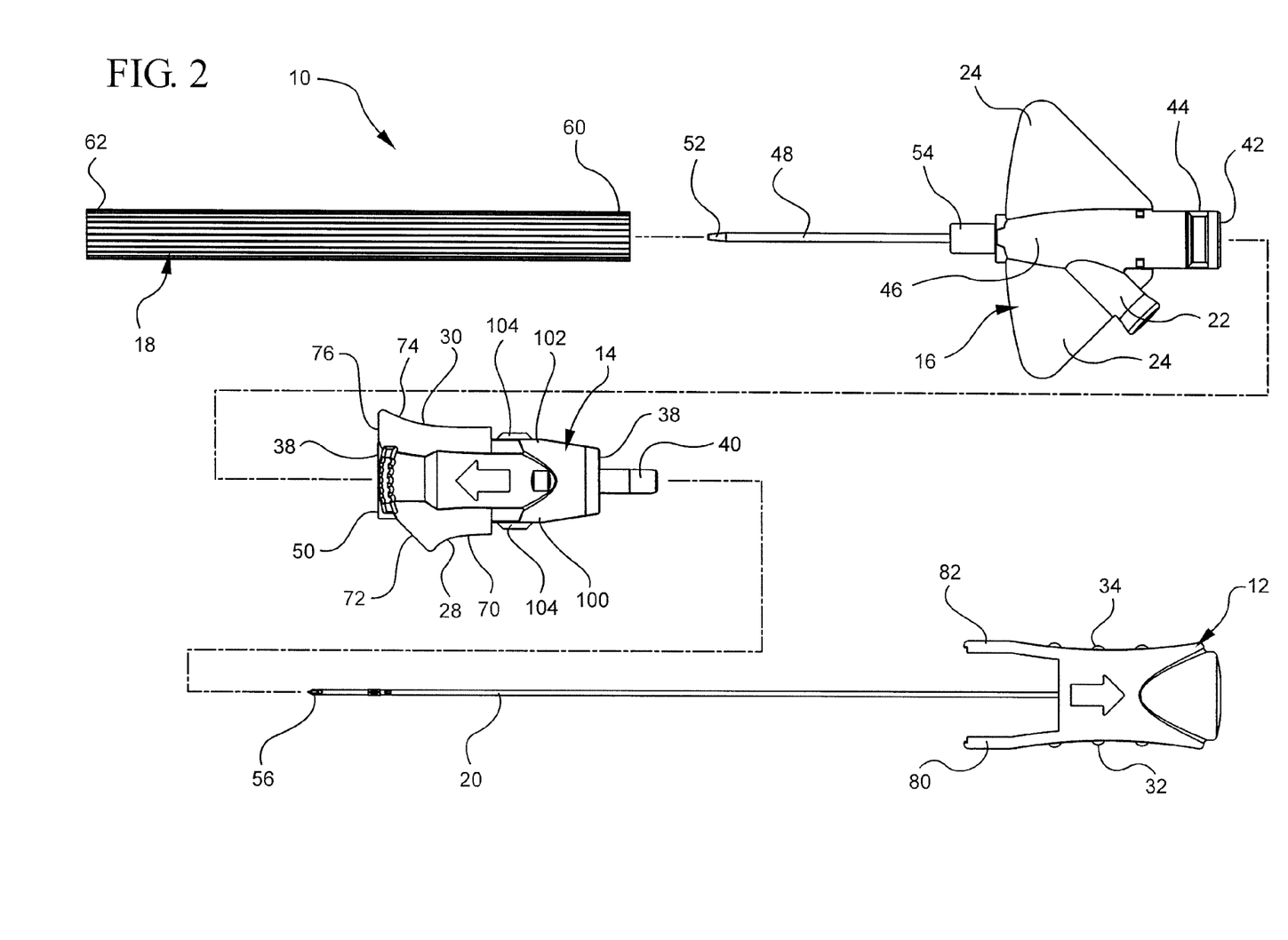
FIG. 2 is an expanded top view of the catheter assembly.

Referring now to FIGS. 1 and 2, a catheter assembly 10 is illustrated including a needle hub 12, a needle shield 14, a catheter adapter 16, an introducer needle 20, and a needle sheath 18. Each of the components 12, 14, 16, 20 and 18 of the catheter assembly 10 is configured so as to cooperate as an integrated apparatus. As more clearly illustrated in FIG. 2, each of the components 12, 14, 16, 20 and 18 of the catheter assembly 10 comprise individual units with features adapted to provide specific functionality to the catheter assembly 10.

For example, the needle hub 12 may include a first wing portion 80 and a second wing portion 82 for engaging a first side 100 and a second side 102 of the needle shield 14, respectively. The first and second wing portions 80, 82 may also include an alignment groove (not shown) for engaging an alignment tab 104 of the needle shield 14. Additionally, the first and second wing portions 80, 82 may include a first gripping surface 32 and a second gripping surface 34, respectively. The first and second gripping surfaces 32, 34 may include additional features such as a texture or a pattern to improve the efficiency of the gripping surfaces.

As assembled in FIGS. 1 and 4-6, the first and second wing portions 80, 82 align with a first contact surface 74 and a second contact surface 74 of the needle shield 14, respectively. As illustrated, the wing portions 80, 82 and the contact surfaces 70, 72 abut one another within the same plane creating an essentially continuous gripping surface between the needle hub 12 and the needle shield 14. In one embodiment, the needle shield 14 comprises a first color, and the needle hub 12 comprises a second, contrasting color, thereby providing a visual indicator that the needle shield 14 and the needle hub 12 are separate components of the catheter assembly 10.

However, the wing portions 80, 82 and the contact surfaces 70, 72 are not continuous or connected as discussed in greater detail below.

Additionally, the needle shield 14 includes a needle port 40 for receiving the introducer needle 20 of the needle hub 12. The needle port 40 extends through the needle shield 14 from a first end 36 to a second end 38 such that the introducer needle 20 of the needle hub 12 may extend through the needle shield 14. The needle shield 14 may also be configured to include a safety feature, such as a needle tip retention device or a safety clip. The safety feature may also include means for maintaining a connection between the needle shield 14 and other components of the catheter assembly 10.

With continued reference to FIGS. 1 and 2, the needle shield 14 may also include a catheter adapter hub 50 for receiving or engaging a first end 44 of the catheter adapter 16. The first end 44 of the catheter adapter 16 is further configured to include a needle port 42 for receiving the introducer needle 20 in a similar fashion to the needle port 40. Additionally, the first end 44 of the catheter adapter 16 may include any feature for compatibly engaging the catheter adapter hub 50 as well as any feature to accommodate a safety function of the needle shield 14.

The catheter adapter 16 is further configured to include a catheter adapter body 46 and a catheter 48. As assembled in FIG. 1, the introducer needle 20 extends through the needle port 42, the catheter adapter body 46 and the catheter 48 whereupon a beveled portion of the needle tip 56 extends beyond the tip 52 of the catheter 48. As configured, the introducer needle 20 is a backbone for the assembled catheter assembly 10 whereby the introducer needle 20 aligns or coordinates each of the individual components 12, 14, 16 of the catheter assembly 10.

The catheter assembly 10 further comprises a needle sheath 18. The needle sheath comprises a first end 60 and a second end 62. The first end 60 is sized and configured to fit over a second end 54 of the catheter adapter 16. Additionally, the second end 62 of the needle sheath 18 is configured to extend beyond a tip 52 of the catheter 48 such that the needle sheath 18 provides protection for both the catheter 48 and the exposed, beveled portion of the needle tip 56.

The catheter adapter 16 may include other features, such as an access port 22, catheter wings 24, or any other feature determined to be beneficial to the operation of the catheter assembly 10. For example, the catheter adapter 16 and the catheter adapter hub 50 may also be modified to include features for interlocking the catheter adapter 16 and the needle shield 14. Additionally, the catheter adapter 16 and the catheter adapter hub 50 may be modified to include a feature for aligning the first end 44 of the catheter adapter 16 within the catheter adapter hub 50, such as by using an alignment tab and an alignment groove. Finally, the access port 22 may be modified to include an infusion source such as a section of intravenous tubing and an intravenous fluid pouch (not shown).

With continued reference to FIGS. 1 and 2, the needle shield 14 comprises a third gripping surface 30 and a fourth gripping surface 28. The third gripping surface 30 is configured to accommodate a first digit, such as an index finger of a user, for gripping the catheter assembly 10. The fourth gripping surface 28 is configured to accommodate a second digit, such as a thumb of a user, for griping the catheter assembly 10. The fourth gripping surface 28 comprises a contact surface 70 and a guard surface 72. The contact surface 70 is configured to accommodate the contour of a user's thumb when griping the catheter assembly 10 during insertion of the catheter 48. The contact surface 70 is further configured and sized to force a first portion of a user's thumb to grip the contact surface 70 and a second portion of a user's thumb to grip the first wing portion 80 of the needle hub 12, simultaneously (see FIGS. 4-6). This simultaneous contact prevents the needle hub 12 and the needle shield 14 from separating due to the linking function of the user's thumb. The guard surface, or feature 72, is positioned between the user's second digit and the catheter adapter 16, to prevent the second digit from contacting the catheter adapter 16. Likewise, the guard feature 76 of the third gripping surface 30 is positioned to prevent the first digit from contacting the catheter adapter 16, as explained in detail below.

Figure 3:
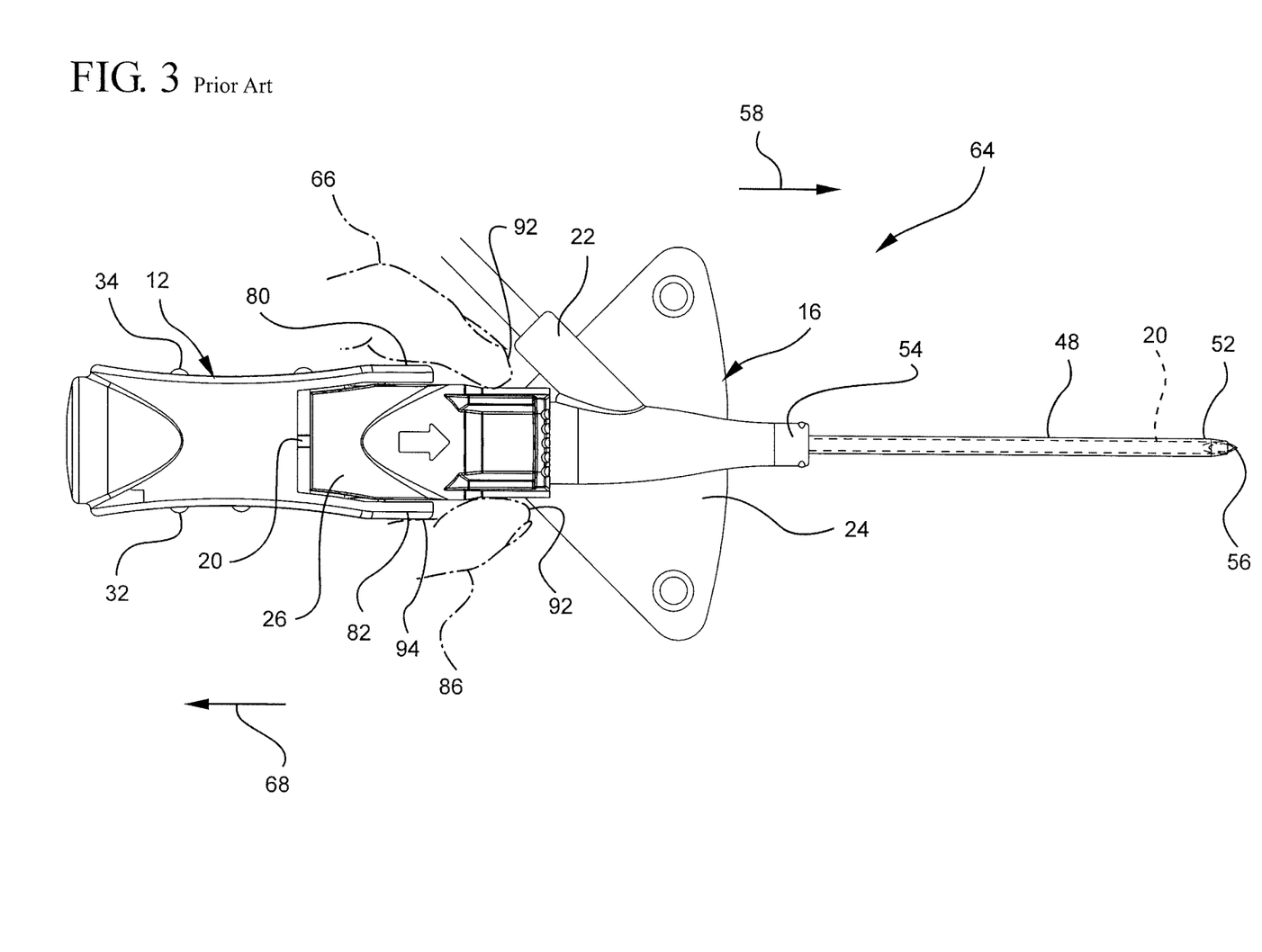
FIG. 3 is a perspective top view of the prior art.

Referring now to FIG. 3, a PRIOR ART catheter assembly 64 is shown. The prior art catheter assembly 64 includes a needle shield 26 which lacks the third and fourth gripping surface described above. While first and second opposing gripping surfaces 32, 34 are provided, common practice entails repositioning a user's thumb 66 and index finger 86 into a "choked up" position as illustrated. The "choked up" position allows for greater control and balance during insertion of the catheter 48. Without a third and fourth gripping surface, a second portion 94 of a user's thumb 66 or index finger 86 may contact the raised edge of the wing portions 80, 82 thereby displacing the needle hub 12 in a direction 68 opposite to the direction 58 of insertion. Upon displacement of the needle hub 12 the beveled portion of the needle tip 56 is withdrawn past the catheter tip 52 resulting in an "over the bevel" condition. When this condition occurs, the beveled portion of the needle tip 56 is unable to sufficiently pierce the patient's skin to provide an opening for introducing the catheter tip 52. As such, this "over the bevel" condition is painful, disruptive, and undesirable during insertion of the needle.

With continued reference to the PRIOR ART of FIG. 3, the needle shield 26 is illustrated without a first or second guard surface. Without a first or second guard surface, a first portion 92 of the user's thumb 66 or index finger 86 may contact the access port 22 and the catheter wing 24 during insertion, respectively. This contact may displace the needle hub 12 in a direction 68 opposite to the direction 58 of insertion. Upon displacement of the needle hub 12, the "over the bevel" condition will occur thereby disrupting the insertion of the catheter 48.

Referring again to FIGS. 1 and 2, the guard surface 72 of the current invention is configured to provide a barrier for preventing a user's thumb from contacting the access port 22 during insertion of the catheter 48. For example, when inserting the catheter 48 into a patient, the user will apply force in a forward direction 58. When the beveled portion of the needle tip 56 contacts the patient, the guard surface 72 will prevent the user's thumb from moving in a forward direction 58 and contacting the access port 22. Without the guard surface 72, as discussed in connection with the PRIOR ART of FIG. 3, a user's thumb 66 is permitted to move in a forward direction 58 and contact the access port 22. Under these circumstances, the force of the user's thumb 66 may advance the catheter adapter 16 in a forward direction 58 to prematurely advance the catheter tip 52 beyond the beveled portion of the needle tip 56 resulting in an "over the bevel" condition. In some implementations of the present invention, the "over the bevel" conditioned is prevented in part by the interposition of guard surfaces 72 and 76 between the user's digits and the various features or parts of the catheter adapter 16.

Figure 4:
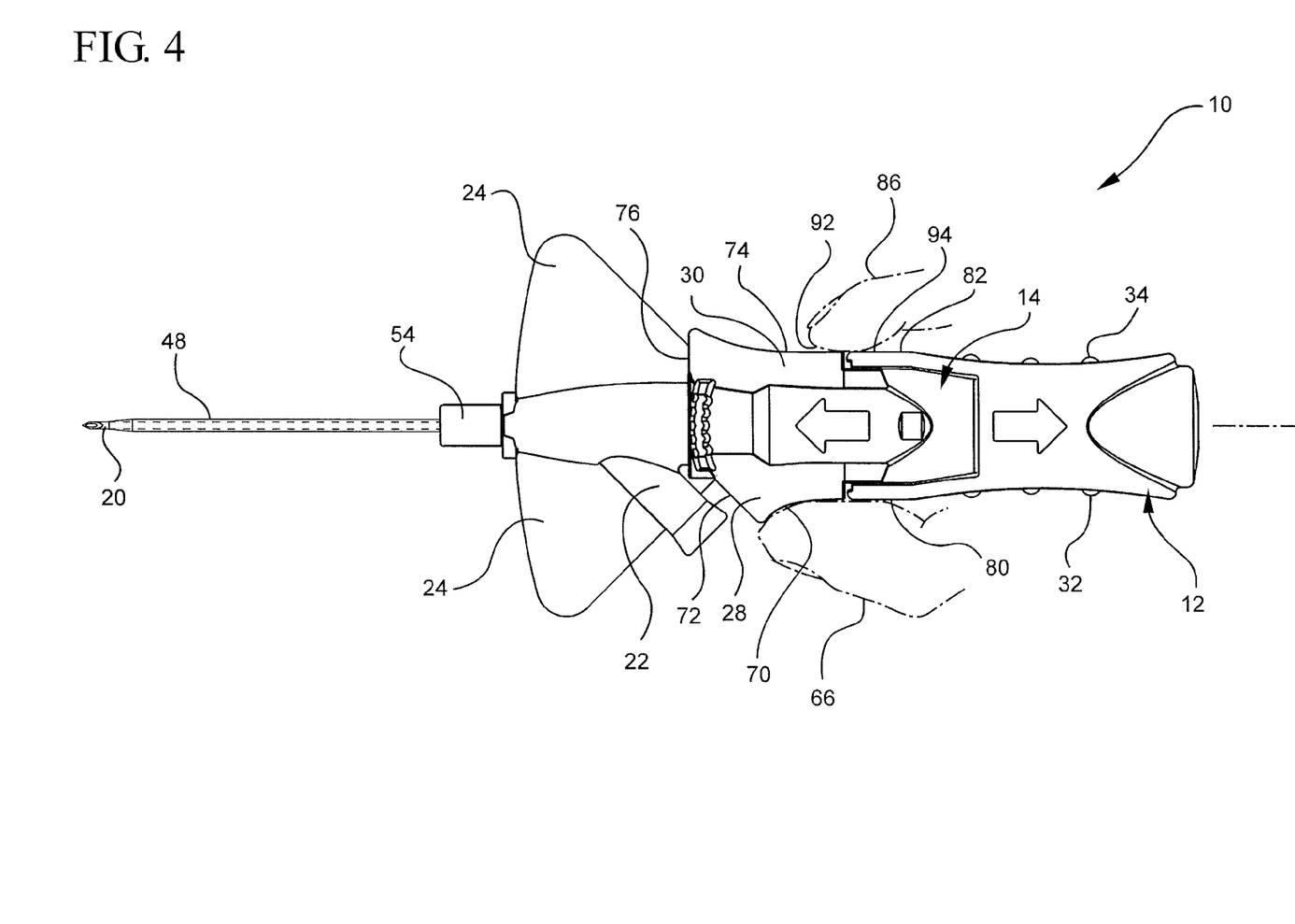
FIG. 4 is a perspective top view of the catheter assembly demonstrating a two-point symmetrical grip.

Referring again to FIGS. 1 and 2, the third gripping surface 30 is configured to accommodate a first digit, such as an index finger, of a user for griping the catheter assembly 10. The third gripping surface 30 comprises a contact surface 74 and a guard surface 76. The contact surface 74 is configured to accommodate the positioning of a user's index finger relative to the position of the user's thumb on the contact surface 70 of the fourth gripping surface 28. For example, as illustrated in FIG. 4, the contact surface 74 permits a user's index finger 86 to be positioned opposite the user's thumb 66 thereby forming a symmetrical grip of the catheter adapter 10. When the needle shield 14 is held in a symmetrical grip, contact surface 74 is further configured and positioned to force a user's index finger 86 to grip both the contact surface 74 and the second wing portion 82 of the needle hub, simultaneously. This simultaneous contact further prevents the needle hub 12 and the needle shield 14 from separating via the linking or bridging function of the user's index finger 86 and thumb 66.

Referring now to FIGS. 1, 2 and 4-6, the guard surface 76 is configured to provide a barrier for preventing the user's index finger 86 from contacting the catheter wing 24 during insertion of the catheter 48. For example, during insertion of the catheter 48 into a patient, the user will apply force in a forward direction 58. When the beveled portion of the needle tip 56 contacts the patient, the guard surface 76 prevents the user's index finger from moving in a forward direction 58 and contacting the catheter wing 24. Without the guard surface 76, as illustrated in the PRIOR ART of FIG. 3, a user's index finger 86 is permitted to move in a forward direction 58 and contact the catheter wing 24. Under this circumstance, the force of the user's index finger 86 may advance the catheter adapter 16 in a forward direction 58 to prematurely advance the catheter tip 52 beyond the beveled portion of the needle tip 56. When this occurs the beveled portion of the needle tip 56 is unable to sufficiently pierce the patient's skin to provide an opening for introducing the catheter 48. Again, this situation results in an "over the bevel" condition as previously discussed. The combination of the two guard surfaces 72, 76 of the current invention prevent the occurrence of the "over the bevel" condition.

Figure 5:
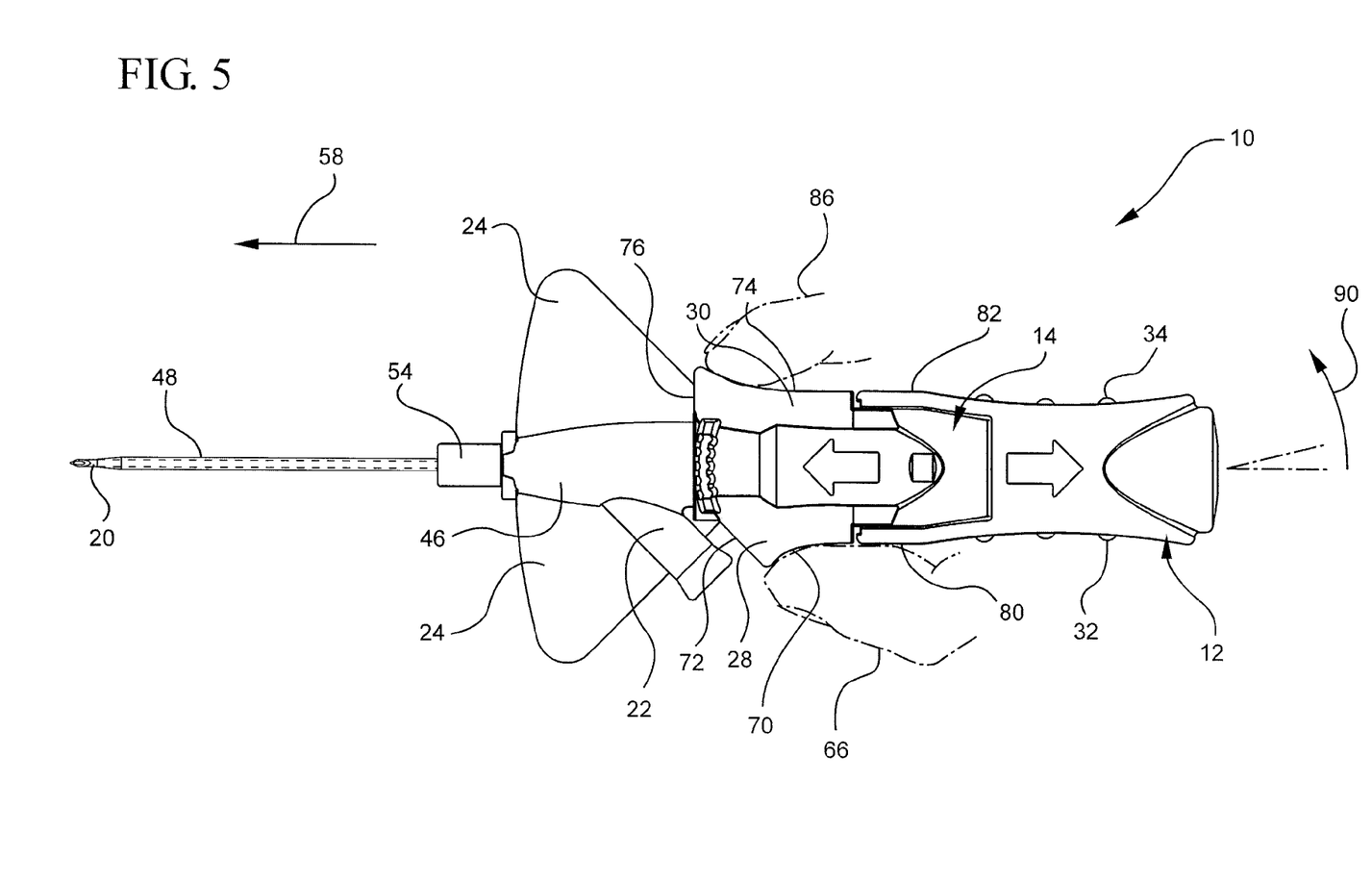
FIG. 5 is a perspective top view of the catheter assembly demonstrating an imbalanced, two-point asymmetrical grip.

The contact surface 74 is further configured to ensure a user's simultaneous contact with the needle shield 14 and the needle hub 12. As illustrated in FIG. 5, the size and configuration of the contact surface 74 may permit a user to grip the contact surface 74 without contacting the second wing portion 82 of the needle hub 12. However, the imbalanced, asymmetrical grip results in a rotational force 90 that is incompatible with insertion procedures for the catheter 48.

With continued reference to FIG. 5, and in accordance with some embodiments of the present invention, several solutions are possible to counteract rotational force 90. A first solution is to reposition the user's index finger 86 to a symmetrical grip as illustrated in FIG. 4. As previously discussed, the symmetrical grip configuration of FIG. 4 ensures a user's simultaneous contact with the needle shield 14 and the needle hub 12. The symmetrical grip configuration prevents the "over the bevel" condition as the user's thumb 66 and index finger 86 performing a linking function between the needle shield 14 and the needle hub 12. Thus, the symmetrical grip configuration prevents an undesirable and premature separation of the needle hub 12 from the needle shield 14.

Figure 6:
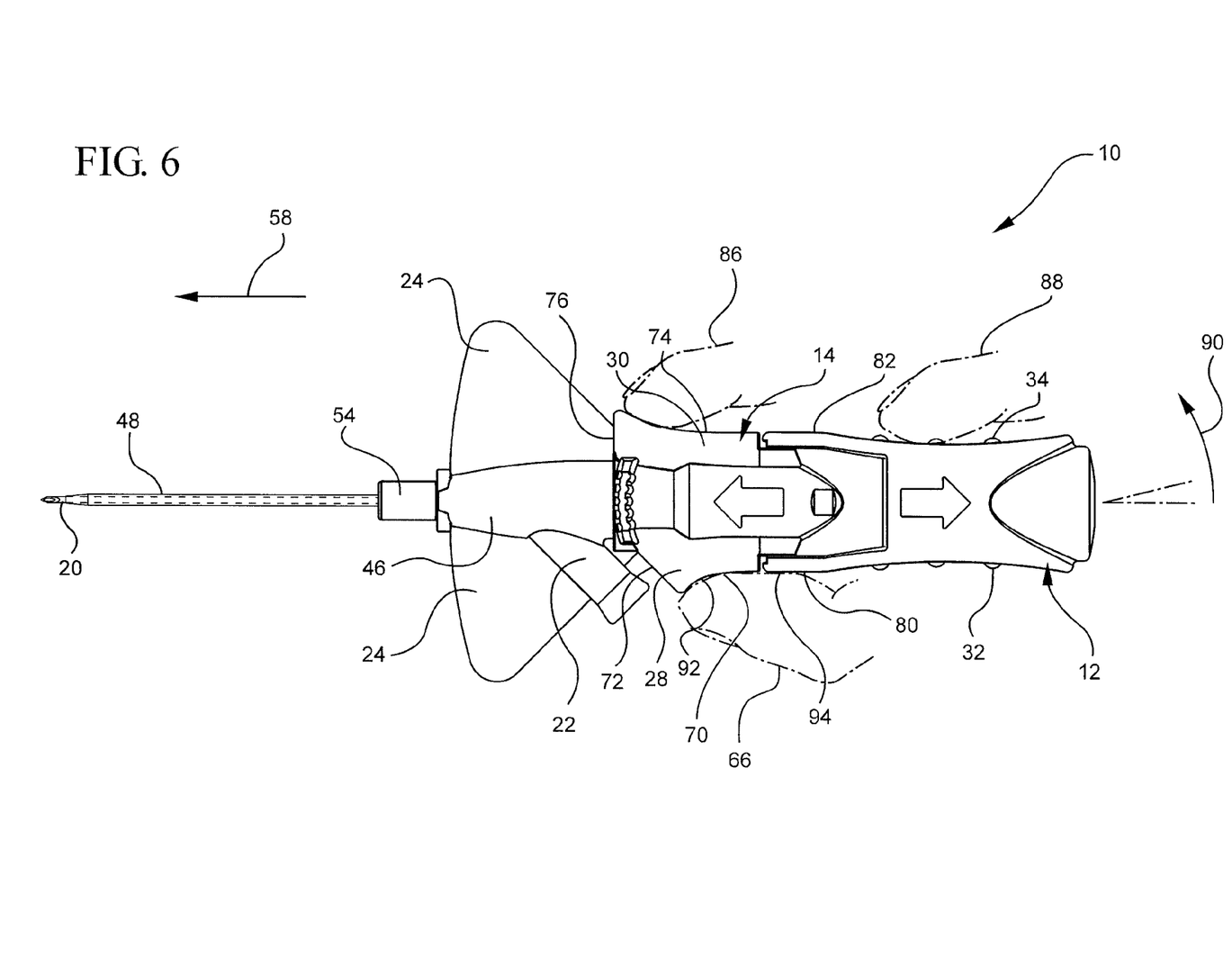
FIG. 6 is a perspective top view of the catheter assembly demonstrating a balanced, three-point asymmetrical grip.

A second solution is illustrated in FIG. 6. As illustrated, the undesirable rotational force 90 is countered or stabilized by the addition of a user's third digit, such as a middle finger 88. The balanced, asymmetrical grip of FIG. 6 is accomplished by positioning a user's middle finger 88 on a second gripping surface 34 as located on the needle hub 12 opposite the first gripping surface 32. The balanced, asymmetrical grip is completed as the user's index finger 86 and thumb 66 are positioned on the third and fourth contact surfaces 74, 70 as illustrated in FIGS. 5 and 6.

The balanced, asymmetrical grip of FIG. 6 prevents the "over the bevel" condition as the user's thumb 66, index finger 86 and middle finger 88 perform a linking function between the needle hub 12 and the needle shield 14. As previously discussed in connection with FIGS. 4 and 5, a first portion 92 of the user's thumb 66 is positioned on the fourth contact surface 70, and a second portion 94 of the user's thumb 66 is positioned on the second gripping surface 32 of the needle hub 12. Again, the position of the user's thumb 66 performs a linking function between the needle hub 12 and the needle shield 14. Furthermore, the user's index finger 86 and middle finger 88 each maintain individual, yet simultaneous contact with the contact surface 74 and first gripping surface 34, respectively. As configured, the user's index finger 86 and middle finger 88 perform a linking function between the needle hub 12 and the needle shield 14 by virtue of the connectedness of the user's hand.

The present gripping surfaces provide a sufficiently balanced gripping position that meets the needs of users within the medical industry. More specifically, the present gripping surfaces provide a user with a "choked up" grip position without the possibility of creating an "over the bevel" condition. Accordingly, the present invention is adapted to provide a useful and safe alternative gripping surface for balanced, controlled handling of catheter assemblies during insertion of a catheter.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. An apparatus comprising:
a catheter adapter;
a needle hub having a first gripping surface and a second gripping surface;
a needle shield having a third gripping surface and a fourth gripping surface for positioning a first digit and a second digit, respectively; and
a needle, wherein the needle extends from the needle hub through the needle shield and through the catheter adapter thereby aligning the catheter adapter, the needle shield and the needle hub along a longitudinal axis into an integrated apparatus;
wherein the fourth gripping surface comprises a proximal end, a distal end, and a curved portion that extends from the proximal end to the distal end, the proximal end being positioned at a first radial distance from the longitudinal axis and the distal end being positioned at a second radial distance from the longitudinal axis, the second radial distance being greater than the first radial distance.

2. The apparatus of claim 1, wherein the third gripping surface comprises a proximal end, a distal end, and a curved portion that extends from the proximal end to the distal end, the proximal end being positioned at a third radial distance from the longitudinal axis and the distal end being positioned at a fourth radial distance from the longitudinal axis, the fourth radial distance being greater than the third radial distance.

3. The apparatus of claim 1, wherein the third gripping surface comprises a proximal end, a distal end, and a curved portion that extends from the proximal end to the distal end, the proximal end being positioned at a third radial distance from the longitudinal axis and the distal end being positioned at a fourth radial distance from the longitudinal axis, the fourth radial distance being substantially the same as the third radial distance.

4. The apparatus of claim 2, wherein the longitudinal position of the distal end of the third gripping surface is different than the longitudinal position of the distal end of the fourth gripping surface.

5. The apparatus of claim 1, wherein the curved portion of the fourth gripping surface is positioned at a distance from the proximal end of the fourth gripping surface such that when a user's thumb is placed on the curved portion, the user's thumb extends proximally past the proximal end onto the first gripping surface.

6. The apparatus of claim 4, wherein the longitudinal position of the distal end of the third gripping surface is nearer to a distal tip of the needle than the distal end of the fourth gripping surface.

7. The apparatus of claim 1, wherein the first gripping surface is positioned at the first radial distance from the longitudinal axis.

8. The apparatus of claim 2, wherein the second gripping surface is positioned at the third radial distance from the longitudinal axis.

9. The apparatus of claim 2, wherein the first and third radial distances are equal.

10. The apparatus of claim 1, wherein a distal end of the curved portion of the fourth gripping surface has a degree of curvature greater than a proximal end of the curved portion of the fourth gripping surface.

11. The apparatus of claim 2, wherein a distal end of the curved portion of the third gripping surface has a degree of curvature greater than a proximal end of the curved portion of the third gripping surface.

12. The apparatus of claim 1, wherein at least one of the third and fourth gripping surfaces further comprises a guard member abutting the catheter adapter.

13. An apparatus comprising:
a catheter adapter;
a needle hub having a first gripping surface and a second gripping surface opposite the first gripping surface;
a needle shield having a third gripping surface and a fourth gripping surface; and
a needle;
wherein the catheter adapter, the needle shield and the needle hub are aligned overtop the needle along a longitudinal axis to form an integrated apparatus;
wherein the fourth gripping surface comprises a proximal end, a distal end, and a curved portion that extends from the proximal end to the distal end, the proximal end being positioned at a first radial distance from the longitudinal axis and the distal end being positioned at a second radial distance from the longitudinal axis, the second radial distance being greater than the first radial distance.

14. The apparatus of claim 13, wherein the third gripping surface comprises a proximal end, a distal end, and a curved portion that extends from the proximal end to the distal end, the proximal end being positioned at a third radial distance from the longitudinal axis and the distal end being positioned at a fourth radial distance from the longitudinal axis, the fourth radial distance being greater than the third radial distance.

15. The apparatus of claim 14, wherein the longitudinal position of the distal end of the third gripping surface is nearer to a distal tip of the needle than the longitudinal position of the distal end of the fourth gripping surface.

16. The apparatus of claim 13, wherein the first gripping surface is positioned at the first radial distance and aligned with the fourth gripping surface.

17. The apparatus of claim 14, wherein the second gripping surface is positioned at the third radial distance and aligned with the third gripping surface.

18. An apparatus comprising:
a catheter adapter;
a needle shield having a third gripping surface and a fourth gripping surface, the needle shield being coupled to the catheter adapter; and
a needle hub coupled to the needle shield;
wherein the catheter adapter, the needle shield and the needle hub are aligned along a longitudinal axis;
wherein the fourth gripping surface comprises a proximal end, a distal end, and a curved portion that extends from the proximal end to the distal end, the proximal end being positioned at a first radial distance from the longitudinal axis and the distal end being positioned at a second radial distance from the longitudinal axis, the second radial distance being greater than the first radial distance.

19. The apparatus of claim 18, wherein the third gripping surface comprises a proximal end, a distal end, and a curved portion that extends from the proximal end to the distal end, the proximal end being positioned at a third radial distance from the longitudinal axis and the distal end being positioned at a fourth radial distance from the longitudinal axis, the fourth radial distance being greater than the third radial distance.

20. The apparatus of claim 19, wherein the longitudinal position of the distal end of the third gripping surface is nearer to a distal end of the catheter adapter than the longitudinal position of the distal end of the fourth gripping surface.

* * * * *